United States Patent [19]

Shernov et al.

[11] Patent Number: 5,304,368
[45] Date of Patent: Apr. 19, 1994

US005304368A

[54] NON-FOAMING, NON-VISCOUS, ALCOHOL-FREE, WATER-BASED, PRESSURIZED HAIR SPRAY PRODUCT

[75] Inventors: Stephen L. Shernov, Long Valley, N.J.; Robert J. Marsh, Malvern, Pa.; Albert Saferstein, Armonk, N.Y.

[73] Assignee: American Telecast Corporation, Paoli, Pa.

[21] Appl. No.: 19,650

[22] Filed: Feb. 19, 1993

[51] Int. Cl.$^5$ ................................. A61K 7/11
[52] U.S. Cl. ................. 424/47; 424/DIG. 1; 424/DIG. 2; 424/71; 424/78.08
[58] Field of Search .................. 424/47, 71, DIG. 1, 424/DIG. 2, 70, 78.08, 45

[56] References Cited

U.S. PATENT DOCUMENTS

| | | | |
|---|---|---|---|
| 4,543,249 | 11/1985 | Nelson | 424/70 |
| 4,845,204 | 7/1989 | Lang et al. | 424/71 |
| 5,053,218 | 10/1991 | Shernov | 424/47 |
| 5,085,859 | 2/1992 | Halloran | 424/71 |
| 5,173,290 | 12/1992 | Halloran | 424/71 |

*Primary Examiner*—Thurman K. Page
*Assistant Examiner*—Raj Bawa

[57] ABSTRACT

A non-foaming, non-viscous, alcohol-free, water-based pressurized hair-fixative spray product for use as the total fill in an aerosol container by delivery from an actuated-valve of predetermined dimensions, particularly the vapor tap and stem orifice sizes.

11 Claims, No Drawings

NON-FOAMING, NON-VISCOUS, ALCOHOL-FREE, WATER-BASED, PRESSURIZED HAIR SPRAY PRODUCT

BACKGROUND OF THE INVENTION

1. Field of the Invention

This invention relates to hair sprays, and more particularly to an alcohol-free, water-based pressurized hair-fixative spray product.

2. Description of the Prior Art

Almost all commercial hair spray compositions contain ethanol as a solvent for the film-forming hair fixative resin. However, ethanol is disfavored because it is a volatile organic compound (VOC) which can pollute the air; also it can give beauticians upper respiratory infections and irritations of the nose and skin; and it is a flammable substance. Accordingly, it is desired to provide a hair spray product which is alcohol-free, i.e., it is a water-based formulation, and which can perform as effectively in commercial use as an ethanol-based product.

Shernov, in U.S. Pat. No. 5,053,218, described a hair spray product including a non-alcohol, one-liquid phase, hair spray composition of shellac, water and dimethyl ether. However, the disclosed system therein produced a hard spray onto the hair of the user, which was considered objectionable because it ruffled the hair. Moreover, it was difficult to maintain a spray of a uniform particle size and composition during evacuation of the entire fill contents of the aerosol can.

Sramek, J., in U.S. Pat. No. 5,068,099, disclosed an aerosol hair spray package having a low delivery rate. However, the hair spray composition used therein was an alcohol-based formulation, there being no more than 10% by water present.

Accordingly, it is desired herein to provide new and improved water-based hair care product for use with a predetermined valve-actuator aerosol packaging system, which combination provides the advantageous performance properties necessary for commercial acceptance of such water-based composition.

SUMMARY OF THE INVENTION

These and other objects and features of the invention are realized herein by the provision of a non-foaming, non-viscous, alcohol-free, water-based pressurized hair-fixative spray product for use as the total fill in an aerosol container by delivery from an actuated-valve of predetermined dimensions, particularly the vapor tap and stem orifice sizes, which consists essentially of:

(a) shellac in the amount of about 0.5 to about 8.0 weight % of the total fill;

(b) a synthetic resin in the amount of about 0.5 to about 8.0 weight % of the total fill;

(c) a neutralizer for said shellac and synthetic resin in the amount of about 0.5 to about 3 weight % of the total fill;

(d) dimethyl ether in an amount in excess of 35 weight % of the total fill; and (e) water in the amount of the rest of the total fill.

In this invention, the excess dimethyl ether in the composition enables the delivery of a fine, soft spray at a predetermined substantially constant spray rate which is of a substantially uniform particle size and composition, without clogging, during delivery of substantially the entire fill contents of the aerosol can at substantially a constant pressure.

The predetermined actuator-valve dimensions include: vapor tap: 0.013 to 0.020 inches; and stem orifice: 0.010 to 0.014 inches. The nozzle orifice is usually about 0.018±10% inches.

The defined composition, in combination with the particular vapor tap and stem orifice dimensions, provides an advantageous spray delivery rate of about 0.20–0.25 g/second. The particle size of the spray herein is 50±10 microns.

DETAILED DESCRIPTION OF THE INVENTION

1. Hair Spray Composition

A. Essential Components

In accordance with the present invention, the non-foaming, non-viscous, alcohol-free, water-based, pressurized hair spray product has the following hair spray formulation in the total fill:

TABLE I

| Essential Components | Suitable | Weight % Preferred | Optimum |
|---|---|---|---|
| (a) Shellac | 0.5–8 | 1.25–7 | 2.5–3.5 |
| (b) Synthetic Resin | 0.5–8 | 2–7 | 5.5–6.5 |
| (c) Neutralizer | 0.5–3 | 1–2.75 | 1.5–2.25 |
| (d) Propellant | excess of 35 | 38–50 | 38–40 |
| (e) Water | rest | rest | rest |

B. Optional Components

Optionally, a plasticizer is present in the composition in an amount up to about 7 weight % of the total fill, generally about 1–5 weight %.

The product also may include, if desired, about 0.1–0.5 weight % of the total fill of one or more of a perfume oil, a fragrance, an antimicrobial agent, a biocidal agent, a buffer, an antioxidant, a coloring agent, an anticorrosive agent, an aloe plant extract, or mixtures thereof.

The pH of the formulation usually is about 9.

C. Detailed Description of the Essential Components (a) Shellac

Shellac refers to all forms and grades of purified lac, which is the hardened resinous secretion of the female, small, scale insect *Laccifer Lacca* (Kerr) of the coccidae family. India, Burma, and Thailand are commercial sources.

Shellac has many grades and forms. In commerce there are two general types of products from the original seedlac: chemically bleached, white shellac and orange flake shellac. Each of these categories of product may be dewaxed to remove about 5% normal wax content. The dewaxed orange flake may also be decolorized. Grades intended for food, drug, or cosmetic use are further processed to meet FDA specifications. In comparison with synthetic polymers or copolymers of the addition type, the molecular weight of shellac is not as high, hence it may better be termed a resin. The molecular weight may be in the range of about 300 to about 3,000. All grades and types of shellac are useful in the present invention. Dewaxed grades are preferred, and food-grade, bleached, dewaxed grades are more preferred.

More particularly, shellac is a mixture of polyhydroxy, mostly aliphatic acids in the form of lactones, lactides, and inter-esters. The mean molecular weight of these compounds is about 1,000. The acidic groups average $1.8 \times 10^{-5}$ in their ionization constants. For each carboxyl group, there are five hydroxyl and three ester groups. Shellac also is non-hydroscopic. It is made more water-soluble by neutralizing with mild bases. The presence of strong alkalis in the formulation would be detrimental to the hair. It is not desirable to neutralize the shellac totally because then the resulting film fixing the hair would not be resistant to high humidity. Ultimately the consumer wishes the hair fixative to be washable from the hair.

(b) Synthetic Resin

The synthetic resin in the formulation of the invention may be selected from among those polymers known as fixatives in the art of hair spray resin compositions, including the resins described in the following U.S. Pat. Nos.: 3,405,084; 3,577,517; 3,726,288; 3,810,977; 3,862,306; 3,927,199; 3,981,987; 4,059,688; 4,164,562; 4,192,861; 4,196,190; 4,237,253; 4,243,548; 4,315,910; 4,348,380; 4,358,567; 4,521,404; 4,543,249; 4,567,035; 4,689,379; 4,767,613; 4,874,604; 4,897,262; 4,923,695; 4,954,336 and 5,021,238. Such resins are suitable candidates for use in this invention, and the disclosures in these patents are incorporated by reference herein. A particularly useful fixative resin is the polymer sold under the trademark AMPHOMER by National Starch and Chemical Corporation which has the CTFA name of Octylacrylamide/Acrylates/-Butylaminoethyl Methacrylate Copolymer, e.g. AMPHOMER ® LV-71, and is described in U.S. Pat. No. 4,192,861 as being a polymer of N-t-octyl acrylamide, methyl methacrylate, hydroxypropyl methacrylate, acrylic acid and t-butyl aminoethyl methacrylate.

(c) Neutralizer

The neutralizer for the shellac and synthetic resin suitably is selected from ammonia, morpholine, dodecylamine, triisopropanolamine, 2-amino-2-methyl-1-propanol (AMP), amino methylpropanediol, amino ethylpropanediol and borax.

(d) Propellant

The propellant for carrying out the present invention is dimethyl ether (DME). Small amounts of other propellants may also be present but that condition is less preferred. At ambient temperature (25° C./70° F.), DME is 35% soluble in water, and water is 6% soluble in DME. In this invention, DME is present in excess of 35%, preferably 38-50%, and most preferably about 38-40%, by weight of the total fill.

(e) Water

Substantially the remainder of the formulation is deionized water.

D. Detailed Description of Optional Components

In order to avoid flaking of the film-forming polymer, or too high a holding power, which might make the hair difficult to brush or comb, a plasticizer may be added to the formulation. A perfume oil, if present in the composition, may also function as a plasticizer for the resin, thus making it less brittle. Numerous plasticizers are available for shellac and the synthetic resin including lanolins, silicones, benzyl alcohol or benzoate, glycerol, phosphate esters, citrate esters, polyethylene glycols, polypropylene glycols, as well as derivatives or mixtures of the above. Preferred plasticizers are polyethylene glycol 15, cocamine phosphate oleate, panthenol, lanolin, dimethylstearamine, polyethylene glycol 75, dimethicone copolyol, laureamide diethyl amine, coconut oils or other vegetable oils and perfume oils or fragrances.

Various polypeptides or proteins such as collagen or its derivatives, or casein derivatives, or albumin derivatives also can have a plasticizing function in the composition as well as adding a desired "crispness" to the film-forming fixative resin. Aliphatic esters such as fatty isopropyl myristates or diisopropyl adipate also can provide added gloss to the hair as well as plasticizing the film-forming resin present in the composition.

E. Detailed Description of Preferred Embodiment of Invention

| Hair Spray Concentrate* | |
|---|---|
| Component | Parts by Weight |
| Amphomer ® LV-71 | 6.12 |
| Shellac | 3.00 |
| AMP 95 | 2.13 |
| Deionized Water | 82.00 |
| Borax | 0.20 |
| Perfume | 0.25 |
| Dimethicone | 0.80 |
| Lanapeg 15 | 5.35 |
| Aloe | 0.05 |
| Panthenol | 0.05 |
| Benzophenone-4 | 0.05 |

Vessel A
1. 60.0 g. water, heat to 150° F.;
2. Add 1.38 g. AMP 95, mix until uniform; and
3. Add 6.12 g. Amphomer LV-71 slowly, mix until dissolved.

Vessel B
1. 22.0 g. water, heat to 130° F.;
2. Add 0.75 g. AMP 95, mix uniformly;
3. Add borax, mix until dissolved;
4. Add Aloe, benzophenone-4 and Panthenol, mix until dissolved.
5. Slowly add the shellac resin, until dissolved with mixing.

Vessel C
1. Add dimethicone, Lanapeg 15 and perfume. Mix until uniform.

Add Vessel B to Vessel A with moderate stirring until uniform. Then add Vessel C to the mixture of A and B after A and B Vessel are cooled to 105° F.

*Procedure for Preparation of Hair Spray Concentrate

F. Preparation of Hair Spray Product

Hair Spray Formulation (Total Fill) = 60% Concentrate + 40% DME

The commercial hair spray products were prepared from 150 g. of the above concentrate which was poured into each of four "8 oz" (53 mm × 185 mm) aluminum cans (300 ml). Then, employing a 1-1 gas buret, 75 g. of dimethyl ether was added to each can, which had previously been fitted with a Seaquist NS-34 valve having the following dimensions:
Stem orifice: 0.011"
Vapor tap: 0.016"
Capillary tubing ID: 0.040"

Each container was then fitted with a Seaquist Misty actuator having a 0.018-inch exit orifice.

A test spray was made from each container to ensure a suitable conical spray at a distance of 27 cm (one foot). The spray rate was about 0.4 g/second. The particle size of the spray was about 50 microns.

After the test spray, each container was capped with a Berry Co. 53-DSA 53-mm double shell plastic closure.

The invention will now be described with reference to the following working example.

EXAMPLE

The pressurized hair-fixative aerosol spray, as produced in the preferred embodiment above, was then tested for percent curl retention, as follows.

A standard hair swatch sample was prepared from 3 g. of 30 cm hair tress bound tightly at one end with a string. This swatch was shampooed, rinsed, and damp-dried with paper towels. Drying was then completed with a conventional hair drier at a distance of 27 cm for 15 minutes, followed by warming in an oven at 40° C. for another 15 minutes, and combed.

The swatch was then sprayed at a distance of 27 cm for 10 seconds with the spray from the product of Example 1, with movement of the spray up and down from all sides. Then the swatch was combed twice, rolled on an open mesh hair roller, and secured with a conventional roller clip. This curled swatch was then dried with a conventional hair drier at a distance of 14 cm for 15 minutes.

The dried, curled swatch was then removed from the curler and the distance measured from the tie at one end to the bottom of the curl. Then the suspended swatch was placed in a chamber at a constant humidity of 96-98% relative humidity at 78° F. for ten minutes. Upon removal from the chamber, the length from the tie to the bottom of the curl was measured again.

Employing the preferred product on ten different hair samples, it was found that percent curl retention varied from 75 to 85%.

Also the combability, the feel, sheen, luster, flaking after two combings, and amount of static charge were all evaluated and found to be satisfactory.

The advantageous features of the invention were recognized during several salon testings of the hair spray product herein against seven commercial aerosol and pump hair sprays, including both water and alcohol-containing formulations. The water-based compositions of this invention were considered the hair spray product of choice by these salon operators.

During application of the hair spray product, the pressure in the can, the spray rate and the particle size of the spray particles were measured at various periods during evacuation of substantially the entire fill in the can. The results are shown in the Table below.

These results demonstrate that the pressure and spray rate remains substantially constant during delivery of substantially the entire fill contents of the can. Furthermore the particle size of the hair sprays delivered from substantially the entire contents of the can are much improved over the related New Idea ® commercial product.

G. Detailed Description of Functional Features of Invention

In this invention, the excess DME, which floats on the water component of the composition, provides a source of propellant vapor to propel the composition through the predetermined vapor tap in the valve-actuator packaging to provide a soft spray without valve clogging. Furthermore, it enables the formation of a uniform spray composition and uniform, fine spray particles during evacuation of the entire fill contents of the can; its presence also provides a relatively dry spray which decreases the drying time of the water-based spray.

The liquid phase of DME that floats on top of the water phase thus provides a source of propellant vapor that only goes through the vapor tap since it has no access to the dip tube at the bottom of the can. A small amount of this liquid phase floating on top of the water phase also can enter into the water phase to maintain the maximum amount of DME in solution with the water. When the valve is activated the water phase comes out of the can via the dip tube. At the same time, some vapor from the propellant in solution with the water will escape as vapor through the vapor tap. That "in solution" propellant thus is drawn from the can in two ways.

1. Liquid through the dip tube.
2. Vapor through the vapor tap, which changes the % of propellant in solution with the water phase because a disproportionate amount of DME is removed in the form of vapor. Without a no vapor tap in the valve-actuator packaging, the solution of 34% DME and 66% water would come out through the dip tube leaving the same percentage in the can. However, the presence of the vapor tap changes this situation because DME vapor is removed also through the vapor tap. The larger the vapor tap opening, the greater the change in the composition of the water-DME solution. Furthermore, the smaller the dimension of the valve stem controlling the amount of liquid coming out of the can, the greater will be the change in the solution composition.

TABLE

| | HAIR SPRAY PRODUCT OF INVENTION | | | |
|---|---|---|---|---|
| Amount in Can | Pressure (psig) | Spray Rate (g/sec) | Particle Size Median Value D (V, 0.5)* (microns) | Particle Size Mean Diameter D (4, 3)** (microns) |
| Full | 65 | 0.22 | 37.1 | 46.6 |
| ¾ | 64 | 0.24 | 38.4 | 48.5 |
| ½ | 63 | 0.23 | 41.2 | 51.4 |
| ¼ | 61 | 0.21 | 42.8 | 56.5 |
| Average | 63 | 0.225 | 39.8 | 50.7 |
| | % Reduction | % Variation | % Increase | % Increase |
| | −6% | 10% | +15.4% | +21.2% |
| COMPARATIVE HAIR SPRAY PRODUCT | | | | |
| New Idea ® (U.S. Pat. No. 5,053,218) | % Reduction about 100% | % Variation 0.40 to 0.28, −30% | Average 34.5; % Increase +40.1% | Average 50.6; % Increase +61.2% |

*D (V, 0.5) = Median Value of the distribution, i.e., 50% of the particles are smaller than this value.
**D (4, 3) = Mean Diameter derived from the volume distribution.

In this invention, a predetermined ratio of vapor tap to valve stem dimensions assures that the spray delivered is of a small particle size, for fast drying, a low flow rate, for a soft spray, and uniform delivery of spray over the entire contents of the can.

The flow rate of the hair spray is predetermined by the composition of the invention and the selected valve-actuator package used to deliver the aerosol spray. In this invention, a soft spray of uniform fine particles is delivered to the hair of the user so as not to upset the hair during application, and to enable the aqueous hair spray to dry quickly. The particle size and composition of the spray also is maintained substantially constant during evacuation of the entire fill contents of the can without any deleterious foaming during the process, and without clogging the orifices in the delivery package.

The predetermined delivery rate for the hair spray composition of the invention is about 0.20–0.25 g/second, at a particle size of about 50±12 microns for a composition containing 60% by weight of the concentrate and 40% by weight of DME. The valve-actuator package preferably has a predetermined vapor tap dimension of 0.013 to 0.020 inches, and a stem orifice of 0.010 to 0.020 inches. The nozzle orifice on the actuator suitably has a dimension of 0.018±10% inches.

The combination of (a) shellac, in the range of about 0.5 to about 8.0 weight %, most preferably about 2–4 weight %, and (b) a synthetic resin, in the amount of about 0.5–8 weight %, most preferably, 5–7 weight %, and, most preferably, in a weight ratio of about (a) to (b) of about 1:2, provided a hair spray composition having significantly increased holding characteristics, reduced viscosity levels, diminished surface tension and no nozzle clogging. As a result, advantageous spray patterns of uniform particle size were obtained.

The amount of neutralizer present in the composition provided sufficient aqueous solubility for both shellac and resin while retaining the desired attributes of washability and curl retention of the aqueous-based composition.

The water component of the composition provided an alcohol-free, water-based composition which solubilized both the neutralized shellac, resin and dimethyl ether materials present in the critical amounts defined and discussed above.

The resulting pH of the system was about 9, which was non-irritating for the user.

While the invention has been described with particular reference to certain embodiments thereof, it will be understood that changes and modifications may be made which are within the skill of the art. Accordingly, it is intended to be bound only by the following claims, in which

What is claimed is:

1. A non-foaming, non-viscous, alcohol-free, water-based, pressurized hair-fixative spray product, including a hair spray composition and a valve-actuated aerosol container having a vapor tap dimension of 0.013 to 0.020 inches, a stem orifice dimension of 0.010 to 0.014 inches and a nozzle orifice dimension of 0.018±10% inches, wherein said hair spray composition has a pH of about 9 and consists essentially of:
   (a) shellac having a molecular weight of about 300 to 3,000, in the amount of about 0.5 to about 8.0 weight % of the total fill;
   (b) a synthetic resin which is an octylacrylamide/acrylate/butyl-aminoethyl methacrylate copolymer in the amount of about 0.5 to about 8.0 weight % of the total fill;
   (c) a neutralizer for said shellac and resin selected from ammonia, morpholine, dodecylamine, triisopropanolamine, 2-amino-2-methyl-1-propanol, aminomethylpropanediol, aminoethylpropanediol and borax in the amount of about 0.5 to about 3 weight % of the total fill;
   (d) dimethyl ether in the amount in excess of 35 weight % of the total fill; and
   (e) water in the amount of the rest of the total fill;
   the presence of said excess dimethyl ether providing a source of propellant vapor to deliver a fine, relatively dry spray of substantially uniform particle size and composition from substantially the entire fill contents in the container.

2. A product according to claim 1 wherein said dimethyl ether is present in an amount of 35-% by weight.

3. A product according to claim 1 wherein the spray delivery rate is about 0.20–0.25 g/second and the particle size of the spray is about 50±10 microns.

4. A hair spray product as in claim 1, wherein the shellac is selected from the group consisting of seed lac, bleached white shellac, dewaxed bleached white shellac, orange flake shellac, dewaxed orange flake shellac, decolorized dewaxed orange flake shellac, food grade shellac, cosmetic grade shellac, and mixtures thereof.

5. A hair spray product as in claim 1, further including a plasticizer in an amount of up to about 7 weight % of the total fill.

6. A hair spray product as in claim 1, wherein the pH of the fill is about 9.

7. A hair spray product as in claim 1, which also includes about 0.1 to about 0.5 weight % of the total fill of one or more of each of the additives selected from the group consisting of a perfume oil, a fragrance, a buffer, an antioxidant, a coloring agent, or mixtures thereof.

8. A hair spray product as in claim 1, wherein (a) is 1.25–7 weight %; (b) is 2–7 weight %; and (d) is 35–50 weight %.

9. A hair spray product as in claim 1, wherein (a) is 2.5–3.5 weight %; (b) is 5.5–6.5 weight %; and (d) is 38–40 weight %.

10. A hair spray product as in claim 1, where the weight ratio of (a) to (b) is about 1:2.

11. A hair spray product as in claim 1, where the pressure delivered and the particle size of the spray is substantially constant during delivery of substantially the entire contents of the fill of the can.

* * * * *